US009488558B2

(12) United States Patent
Cao et al.

(10) Patent No.: US 9,488,558 B2
(45) Date of Patent: Nov. 8, 2016

(54) DEVICE AND METHOD FOR DETECTING THE TENSION ON A GUIDE ROPE OF A HANGING SCAFFOLD IN A CONSTRUCTION SHAFT

(71) Applicant: CHINA UNIVERSITY OF MINING AND TECHNOLOGY, Xuzhou, Jiangsu (CN)

(72) Inventors: Guohua Cao, Xuzhou (CN); Yandong Wang, Xuzhou (CN); Zhencai Zhu, Xuzhou (CN); Weihong Peng, Xuzhou (CN); Jinjie Wang, Xuzhou (CN); Shanzeng Liu, Xuzhou (CN); Gang Shen, Xuzhou (CN); Hao Lu, Xuzhou (CN)

(73) Assignee: CHINA UNIVERSITY OF MINING AND TECHNOLOGY, Xuzhou, Jiangsu (CN)

( * ) Notice: Subject to any disclaimer, the term of this patent is extended or adjusted under 35 U.S.C. 154(b) by 34 days.

(21) Appl. No.: 14/411,080

(22) PCT Filed: Jun. 5, 2014

(86) PCT No.: PCT/CN2014/079201
§ 371 (c)(1),
(2) Date: Dec. 23, 2014

(87) PCT Pub. No.: WO2015/100937
PCT Pub. Date: Jul. 9, 2015

(65) Prior Publication Data
US 2016/0109341 A1    Apr. 21, 2016

(30) Foreign Application Priority Data
Jan. 3, 2014  (CN) .......................... 2014 1 0003998

(51) Int. Cl.
*G01N 3/00*    (2006.01)
*G01N 11/00*    (2006.01)
(Continued)

(52) U.S. Cl.
CPC *G01N 3/08* (2013.01); *B66D 1/50* (2013.01); *B66D 1/605* (2013.01); *G01L 5/103* (2013.01); *G01L 5/108* (2013.01)

(58) Field of Classification Search
None
See application file for complete search history.

(56) References Cited

U.S. PATENT DOCUMENTS 6,079,576 A * 6/2000 Bosler ...................... B66D 1/44
                                                    212/278
6,345,724 B1 * 2/2002 Masumoto .............. B66C 11/20
                                                    212/173
(Continued)

FOREIGN PATENT DOCUMENTS

CN    101762351 A    6/2010
CN    201567177 U    9/2010
(Continued)

OTHER PUBLICATIONS

Shao, Xingguo et al., "Auto-leveling control for sinking winch mechanism and experimental validation", Journal of China Coal Society, No. 3, vol. 37, Mar. 2012, pp. 528-532, China.
(Continued)

*Primary Examiner* — Andre Allen
*Assistant Examiner* — Jermaine Jenkins
(74) *Attorney, Agent, or Firm* — Millman IP Inc.

(57) ABSTRACT

The present invention discloses a device and a method for detecting the tension on a guide rope of a hanging scaffold in a construction shaft. The guide rope is released by a winch, rounds over a hoisting sheave, is connected to the hanging scaffold, and then is tensioned up; the hoisting sheave is disposed at a position above the winch, and the device comprises a slide device, two tension ropes, and a pull rope, wherein the slide device is fitted around the guide rope, the two tension ropes are fixed to the two sides of the slide device respectively and arranged parallel to the guide rope, the pull rope is fixed to the lower part of the slide device and arranged perpendicular to the guide rope. On the basis of the basic principles of mechanics, the force applied on the guide rope can be calculated indirectly according to the proportional relation between the forces applied on the tension rope and guide rope and the lengths of the ropes. The device disclosed in the present invention is simple, and the method disclosed in the present invention is skillful. The device and method are applicable to thick and thin steel wire ropes and highly universal, and are low in cost.

8 Claims, 4 Drawing Sheets

(51) Int. Cl.
*G01N 3/08* (2006.01)
*B66D 1/50* (2006.01)
*B66D 1/60* (2006.01)
*G01L 5/10* (2006.01)

(56) References Cited

U.S. PATENT DOCUMENTS

| | | | | |
|---|---|---|---|---|
| 6,367,757 | B1* | 4/2002 | Aramaki | E04B 9/006 248/327 |
| 6,439,407 | B1* | 8/2002 | Jacoff | B66C 13/08 212/272 |
| 6,901,818 | B1* | 6/2005 | Cheung | G01L 5/10 114/230.1 |
| 8,418,814 | B1* | 4/2013 | Byers | B66D 1/54 182/144 |
| 2003/0205703 | A1* | 11/2003 | McCormick | B66B 1/32 254/267 |
| 2004/0094497 | A1* | 5/2004 | Oja | B66C 13/06 212/274 |
| 2006/0192188 | A1* | 8/2006 | Sanders | B66D 1/485 254/361 |
| 2007/0272490 | A1* | 11/2007 | Blasek | B66B 9/187 187/254 |
| 2007/0274427 | A1* | 11/2007 | Jullien | B66D 1/58 376/268 |
| 2009/0224221 | A1* | 9/2009 | Monroe | B66C 5/02 254/4 R |
| 2010/0206831 | A1* | 8/2010 | Faust | B66D 1/58 212/278 |
| 2010/0237306 | A1* | 9/2010 | Eschelbacher | B66D 1/12 254/362 |
| 2011/0251803 | A1 | 10/2011 | Teurlay et al. | |

FOREIGN PATENT DOCUMENTS

| | | |
|---|---|---|
| CN | 102602838 | 7/2012 |
| CN | 102661856 A | 9/2012 |
| CN | 202499676 U | 10/2012 |
| CN | 103359645 A | 10/2013 |
| CN | 103776577 A | 5/2014 |
| JP | 58156824 A | 9/1983 |

OTHER PUBLICATIONS

PCT/CN2014/079201, International Search Report, Aug. 13, 2014.
CA2885620, Canadian Office Action, Feb. 26, 2016.

\* cited by examiner

DEVICE AND METHOD FOR DETECTING THE TENSION ON A GUIDE ROPE OF A HANGING SCAFFOLD IN A CONSTRUCTION SHAFT

FIELD OF THE INVENTION

The present invention relates to a construction shaft system, in particular to a device and a method for detecting the tension on a guide rope of a hanging scaffold in a construction shaft.

BACKGROUND OF THE INVENTION

As the hanging scaffold in a construction shaft system is lowered with the construction progress, the distance from the hanging scaffold to the shaft mouth increases gradually, the operating conditions become more complex, and the ambient environment of the hanging scaffold is very damp. To detect the suspension force of the hanging scaffold, if a tension sensor is added at the joint between the guide rope and the hanging scaffold, the guide rope has to be removed first, and the tension sensor must meet dust-proof and water-proof requirements. However, since the hanging scaffold is at a deep position in the shaft after a construction period, high tension exists on the guide rope, resulting in high torque on the guide rope; consequently, when the guide rope is removed, it will twist violently and may cause injuries to the workers, and the hanging scaffold may also twist owing to stress imbalance. In addition, to adopt the method that detects the tension on a guide rope by a tension sensor, the tension sensor must be connected to the guide rope or between the guide rope and the hanging scaffold at the early stage of shaft construction; however, in that case, it is difficult to transfer the sensor signal from the down-hole area to the shaft mouth. Besides the method that utilizes a tension sensor, other steel wire rope detection devices mainly include devices that are clamped on the steel wire rope and measure the tension indirectly by measuring the lateral force or the longitudinal strain of the steel wire rope. The former method directs at the tension on a thin steel wire rope, but for a thick suspension rope or guide rope of a hanging scaffold in a construction shaft, due to the short distance and high rigidity, such method has problems that the lateral pressing force is too high and the measurement is inaccurate; in addition, the steel wire rope may be injured owing to the excessive reversed bending. The latter method requires a set of wireless node transmission devices to measure the tension on a steel wire rope of a hoisting system, causing a challenge in terms of the detection cost.

SUMMARY OF THE INVENTION

Technical Problems to be Solved

In view of the drawbacks in the prior art, the present invention provides a device and a method for detecting the tension on a hanging scaffold in a construction shaft, which can solve the problems of the method that utilizes a tension sensor mounted on a guide rope to detect the suspension tension of a hanging scaffold in a construction shaft, such method has high requirement on the tension sensor hardware and the sensor can not be mounted at any time. The device and the method according to the present application can also solve the problems of other detection methods in the prior art that have limited applicability for steel wire ropes in different thicknesses and high cost.

Technical Solution

To solve the technical problems described above, the present invention employs the following technical solution:

A device for detecting the tension on a guide rope of a hanging scaffold in a construction shaft, wherein, the guide rope is released by a winch, rounds over a hoisting sheave, is connected to the hanging scaffold, and then is tensioned up; the hoisting sheave is disposed at a position above the winch, and comprises a slide device, two tension ropes, and a pull rope, the slide device is fitted around the tensioned guide rope, the two tension ropes are fixed to the two sides of the slide device respectively and arranged parallel to the guide rope, the pull rope is fixed to the lower part of the slide device and arranged perpendicular to the guide rope.

Moreover, according to the present invention, the slide device comprises a grooved track roller and two guard plates, the two guard plates are arranged symmetrically at the outer side of the two end faces of the grooved track roller and are hinged to the track roller via a roller pin shaft and a bearing; a connecting shaft is arranged at each side of the guard plate above the guide rope, both of the two connecting shafts pass through the two guard plates, and the two tension ropes are fixed to the connecting shaft at the corresponding side respectively; a third connecting shaft is arranged on the guard plate below the guide rope and passes through the two guard plates respectively, and the pull rope is fixed to the third connecting shaft.

Moreover, according to the present invention, a tension sensor is arranged on the tension rope and the pull rope respectively.

Moreover, according to the present invention, the pull rope is tensioned up by a pull rope reeling device.

Moreover, according to the present invention, the tension ropes are tensioned up by tension rope reeling device, which comprises a drum and two supports arranged at the two sides of the drum, the drum is mounted between the two supports via a shaft, and a locking structure is arranged on one of the supports and on the drum at the same side of the support.

Moreover, according to the present invention, the locking structure comprises a locking ring arranged on one end of the drum and a bolt assembly arranged on the support at the same side, the locking ring has counter bores arranged in circle, the bolt assembly comprises a bolt seat fixed to the support and locking bolts connected to the bolt seat by threaded fitting, and the locking bolts match the counter bores.

Moreover, according to the present invention, a handle ring is arranged on the drum, so that the tension rope can be wound conveniently on the drum.

Moreover, according to the present invention, two tension rope reeling devices are arranged at the outer side of the hoisting sheave and the winch in symmetry to the center point of a connecting line between the hoisting sheave and the winch in the direction of the tension ropes; a shaft encoder is mounted on the shaft. The released length of the tension rope is detected by the shaft encoder, so that the slide device is adjusted to the center point of the guide rope.

A method for detecting the tension on the guide rope of a hanging scaffold in a construction shaft, comprising the following steps executed sequentially:

a. the length of a guide rope between a winch and a hoisting sheave is supposed as l, turning the drum of a tension rope reeling device to release tension ropes, detecting the released length of the tension ropes with a shaft encoder, adjusting a slide device to the center point of the guide rope, and screwing down the locking bolts of a tension rope reeling device into the counter bores in a locking ring;

b. adjusting the position of a pull rope reeling device on the ground, till a pull rope is perpendicular to the guide rope;

c. winding the pull rope on the pull rope reeling device, pulling the slide device to make a displacement x in the direction of the pull rope, and logging the tension $f_1$ on a tension sensor mounted on the tension rope and the tension $f_2$ on a tension sensor mounted on the pull rope;

d. calculating the tension F on the guide rope with a formula $F = f_2 \cdot l/(4x) - f_1$.

Beneficial Effects

According to the present invention, on the basis of the basic principles of mechanics, the force applied on the guide rope can be calculated indirectly according to the proportional relation between the forces applied on the tension rope and guide rope and the length ratio of the ropes, utilizing the ingenious cooperation among the slide device, the tension rope, and the guide rope.

The device and method according to the present invention is applicable to detection of the tension on the guide rope of a hanging scaffold in a construction shaft, detection of the tension on a hanging rope of a hanging scaffold in a construction shaft, and detection of the tension on a steel wire rope in other shaft hoisting systems.

The device according to the present invention is simple in structure, the method according to the present invention is ingenious, and the device and method are applicable to both thin and thick steel wire ropes, and are highly universal and low in cost. The inconveniences incurred by arranging a tension sensor directly on the guide rope are avoided and the drawbacks in other measuring methods in the prior art, such as high requirement on the thickness of the steel wire rope and high cost, etc., are overcome.

DETAILED DESCRIPTION OF THE EMBODIMENTS

Hereunder the present invention will be further detailed, with reference to the accompanying drawings.

Figure 1:
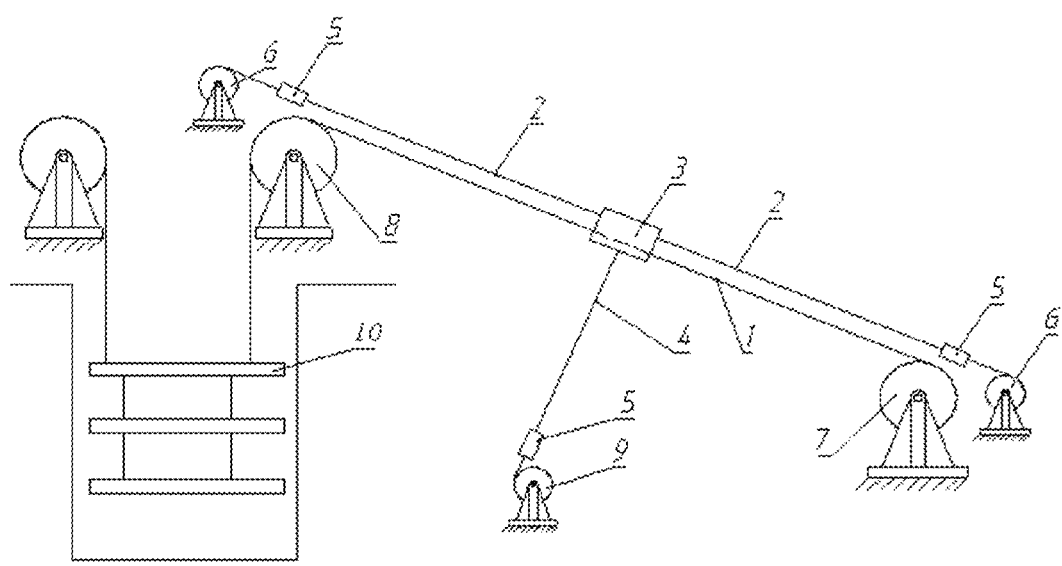
FIG. 1 is a schematic system diagram of the device for detecting the tension on a guide rope according to the present invention.
Figure 2:
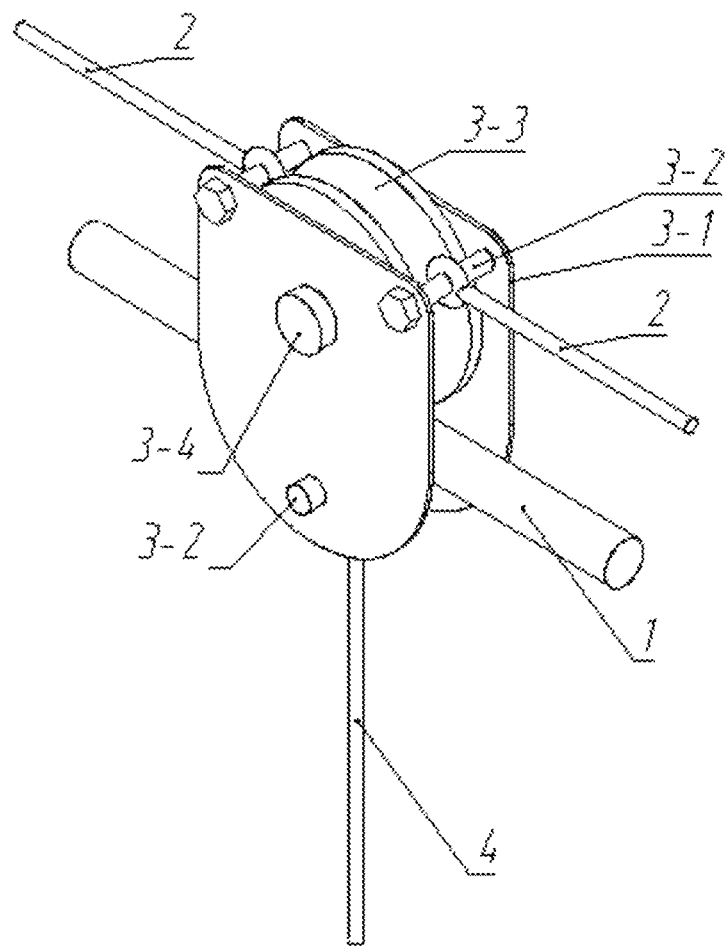
FIG. 2 is a 3D view of the slide device according to the present invention.
Figure 3:
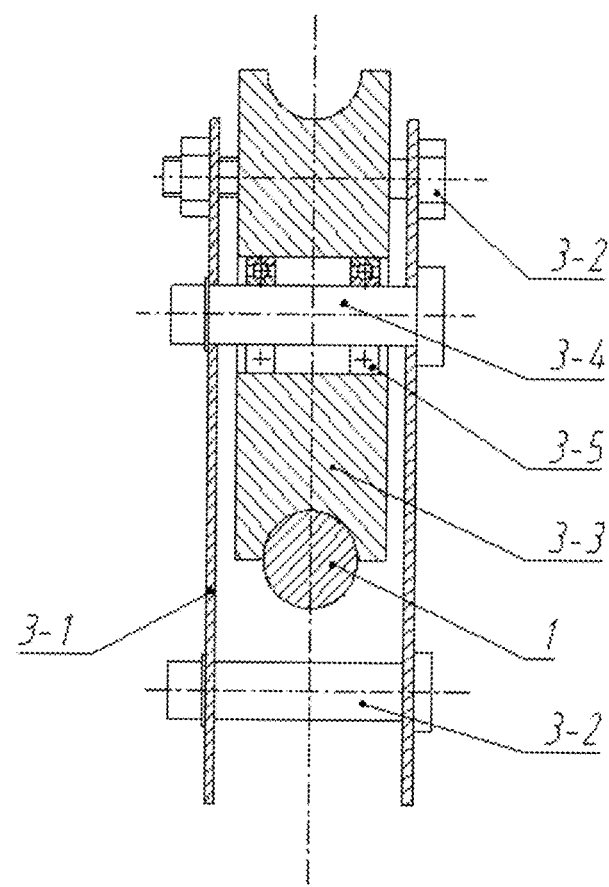
FIG. 3 is sectional view of the slide device shown in FIG. 2.
Figure 4:
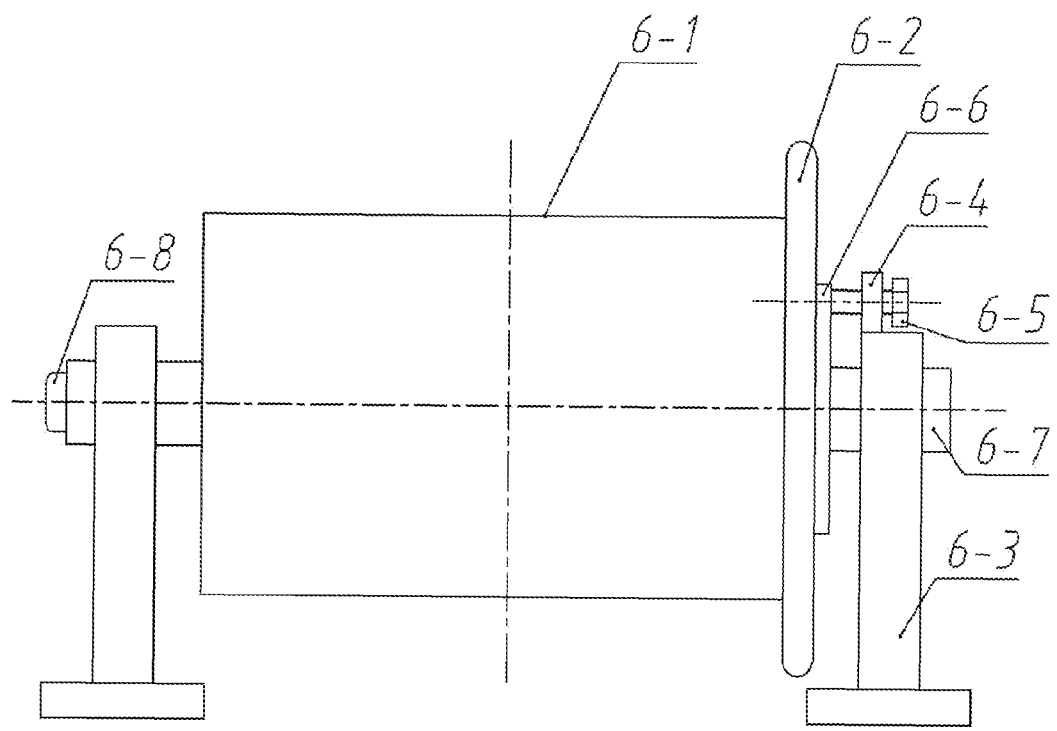
FIG. 4 is a schematic structural diagram of the tension rope reeling device according to the present invention.

As shown in FIG. 1, a device for detecting the tension on the guide rope of a hanging scaffold in a construction shaft is provided, wherein, the guide rope 1 rounds over a winch 7 and a hoisting sheave 8 and then extends into the shaft, one end of the guide rope 1 is connected to a hanging scaffold 10, and the hoisting sheave 8 is positioned above the winch 7. The device further comprises a slide device 3, two tension ropes 2, and a pull rope 4, wherein, a tension sensor 5 is arranged on the tension ropes 2 and the pull rope 4 respectively.

Specifically, the slide device 3 is fitted over the guide rope 1, and comprises a grooved track roller 3-3 and two guard plates 3-1, the two guard plates 3-1 are arranged symmetrically at the outer side of the two end faces of the grooved track roller 3-3 and are hinged to the track roller 3-3 via a roller pin shaft 3-4 and a bearing 3-5; a connecting shaft 3-2 is arranged at the top left corner and top right corner of the guard plate 3-1 above the guide rope 1, and passes through the two guard plates 3-1, and a tension rope 2 is fixed to each of the connecting shafts 3-2 respectively; a third connecting shaft 3-2 is arranged on the guard plate 3-1 below the guide rope 1 and passes through the two guard plates 3-1, and a pull rope 4 is fixed to the third connecting shaft 3-2. The slide device 3 is fitted over the guide rope 1 in the following way: first, removing the third connecting shaft 3-2 from the slide device 3; then, placing the groove of the track roller 3-3 of the slide device 3 on the guide rope 1; next, connecting the removed connecting shaft 3-2 to the slide device 3; finally, fastening the pull rope 4 to the two upper connecting shafts 3-2.

Two tension rope reeling devices 6 are arranged at the outer side of the hoisting sheave 8 and the winch 7 in symmetry to the center point of a connecting line between the hoisting sheave 8 and the winch 7 in the direction of the tension ropes 2, to regulate and tension up the tension ropes 2; the two tension ropes 2 are wound onto the tension rope reeling device 6 at the corresponding side, and are tensioned up by the corresponding tension rope reeling device 6, and are arranged parallel to the guide rope 1. The tension rope reeling device 6 comprises a drum 6-1 and two supports 6-3 arranged at the two sides of the end faces of the drum 6-1, and the drum 6-1 is mounted between the two supports 6-3 via a shaft 6-7 and a bearing. Wherein, a locking structure is arranged on the right support 6-3 and the drum 6-1 at the side of the right support 6-3. The locking structure comprises a locking ring 6-6 arranged on one end of the drum 6-1 and a bolt assembly arranged on the support 6-3 at the same side, the locking ring 6-6 has counter bores arranged in circle, the bolt assembly comprises a bolt seat 6-4 fixed to the support 6-3 and locking bolts 6-5 connected to the bolt seat 6-4 by threaded fitting, and the locking bolts 6-5 match the counter bores. A handle ring 6-2 is hinged to the drum 6-1, so that the tension rope 2 can be wound on the drum 6-1 conveniently. A shaft encoder 6-8 is mounted on the shaft 6-7, to measure the released length of the tension rope 2. After the tension rope 2 is released, the locking bolts are screwed down into the counter bores of the locking ring 6-6 and tightened up, so as to lock up the tension rope reeling device 6 and retain the released length of the tension rope 2.

A pull rope reeling device 9 is arranged below the center point of the connecting line between the hoisting sheave 8 and the winch 7, and the pull rope 4 is wound on the pull rope reeling device 9.

A method for detecting the tension on the guide rope of a hanging scaffold in a construction shaft, comprising the following steps executed sequentially:

a. the length of the guide rope 1 between a winch 7 and a hoisting sheave 8 is supposed as l, turning a drum 6-1 of a tension rope reeling device 6 to release tension ropes 2, detecting the released length of the tension ropes 2 with a shaft encoder 6-8, adjusting a slide device 3 to the center point of the guide rope 1, and screwing down the locking bolts 6-5 of the tension rope reeling device 6 into the counter bores in a locking ring 6-6;
b. adjusting the position of a pull rope reeling device 9 on the ground, till a pull rope 4 is perpendicular to the guide rope 1;
c. winding the pull rope 4 on the pull rope reeling device 9, pulling the slide device 3 to make a displacement x in the direction of the pull rope, and logging the tension $f_1$ on a tension sensor 5 mounted on the tension rope 2 and the tension $f_2$ on a tension sensor 5 mounted on the pull rope 4;
d. calculating the tension F on the guide rope 1 with a formula $F=f_2 \cdot l/(4x)-f_1$.

Since the slide device 3 can slide on the guide rope 1, the slide device 3 will always press the guide rope 1 in the process that the guide rope 1 is reeled up or down, and the slide device 3 will always be at the center point of the connecting line between the winch 7 and the hoisting sheave 8 in that process, so that the tension on the guide rope can be detected in real time.

The device is in a balanced state after the entire movement process. It is seen from the stress analysis of the slide device 3 made on the basis of the force balance principle: the resultant forces of the guide rope 1 and tension ropes 2 and the force on the pull rope 4 constitute a force triangle, since the tension ropes are immobilized, the sides where the resultant forces of the guide rope 1 and tension ropes 2 exist in the force triangle are approximately in constant lengths; thus, the following equation is obtained according to the proportional relation between force and length:

$$\frac{2(f_1 + F)}{\frac{1}{2}l} = \frac{f_2}{x}$$

i.e., the tension F on the guide rope 1 is $F=f_2 \cdot l/(4x)-f_1$.

While the present invention has been illustrated and described with reference to some preferred embodiments, the present invention is not limited to these. Those skilled in the art should recognize that various variations and modifications can be made without departing from the spirit and scope of the present invention. All of such variations and modifications shall be deemed as falling into the protected scope of the present invention.

The invention claimed is:

1. A device for detecting the tension on a guide rope of a hanging scaffold in a construction shaft, wherein, the guide rope (1) is released by a winch (7), rounds over a hoisting sheave (8), is connected to a hanging scaffold (10), and then is tensioned up; the hoisting sheave (8) is disposed at a position above the winch (7), the device comprises a slide device (3), two tension ropes (2), and a pull rope (4), the slide device (3) is fitted around the tensioned guide rope (1), the two tension ropes (2) are fixed to the two sides of the slide device (3) respectively and arranged parallel to the guide rope (1), the pull rope (4) is fixed to the lower part of the slide device (3) and arranged perpendicular to the guide rope (1), wherein, the slide device (3) comprises a grooved track roller (3-3) and two guard plates (3-1), the two guard plates (3-1) are arranged symmetrically at the outer side of the two end faces of the grooved track roller (3-3) and are hinged to the track roller (3-3) via a roller pin shaft (3-4) and a bearing (3-5); a connecting shaft (3-2) is arranged at each side of the guard plate (3-1) above the guide rope (1) respectively, and both of the two connecting shaft (3-2) pass through the two guard plates (3-1), and the two tension ropes (2) are fixed to the connecting shafts (3-2) at the corresponding sides respectively; a third connecting shaft is arranged on the guard plate (3-1) below the guide rope (1) and passes through the two guard plates (3-1) respectively, and the pull rope (4) is fixed to the third connecting shaft.

2. The device for detecting the tension on a guide rope of a hanging scaffold in a construction shaft according to claim 1, wherein, a tension sensor (5) is arranged on the tension ropes (2) and the pull rope (4) respectively.

3. The device for detecting the tension on a guide rope of a hanging scaffold in a construction shaft according to claim 1, wherein, the pull rope is tensioned up by a pull rope reeling device (9).

4. A device for detecting the tension on a guide rope of a hanging scaffold in a construction shaft, wherein, the guide rope (1) is released by a winch (7), rounds over a hoisting sheave (8), is connected to a hanging scaffold (10), and then is tensioned up; the hoisting sheave (8) is disposed at a position above the winch (7), the device comprises a slide device (3), two tension ropes (2), and a pull rope (4), the slide device (3) is fitted around the tensioned guide rope (1), the two tension ropes (2) are fixed to the two sides of the slide device (3) respectively and arranged parallel to the guide rope (1), the pull rope (4) is fixed to the lower part of the slide device (3) and arranged perpendicular to the guide rope (1), wherein, the tension ropes are tensioned up by two tension rope reeling devices, each tension rope reeling device comprises a drum (6-1) and two supports (6-3) arranged at the two sides of the drum (6-1), the drum (6-1) is mounted between the two supports (6-3) via a shaft (6-7), and a locking structure is arranged on one of the supports (6-3) and on the drum (6-1) at the same side of the support (6-3).

5. The device for detecting the tension on a guide rope of a hanging scaffold in a construction shaft according to claim 4, wherein, the locking structure comprises a locking ring (6-6) arranged on one end of the drum (6-1) and a bolt assembly arranged on the support (6-3) at the same side, the locking ring (6-6) has counter bores arranged in circle, the bolt assembly comprises a bolt seat (6-4) fixed to the support (6-3) and locking bolts (6-5) connected to the bolt seat (6-4) by threaded fitting, and the locking bolts (6-5) match the counter bores.

6. The device for detecting the tension on a guide rope of a hanging scaffold in a construction shaft according to claim 4, wherein, a handle ring (6-2) is arranged on the drum (6-1).

7. The device for detecting the tension on a guide rope of a hanging scaffold in a construction shaft according to claim 4, wherein, two tension rope reeling devices (6) are arranged at the outer side of the hoisting sheave (8) and the winch (7) in symmetry to the center point of a connecting line between the hoisting sheave (8) and the winch (7) in the direction of the tension ropes (2); a shaft encoder (6-8) is mounted on the shaft (6-7).

8. A method for detecting the tension on a guide rope of a hanging scaffold in a construction shaft, comprising the following steps executed sequentially:
   a. the length of a guide rope (1) between a winch (7) and a hoisting sheave (8) is supposed as l, turning a drum (6-1) of a tension rope reeling device (6) to release tension ropes (2), detecting the released length of the tension ropes (2) with a shaft encoder (6-8), adjusting a slide device (3) to the center point of the guide rope (1), and screwing down locking bolts (6-5) of the tension rope reeling device (6) into counter bores in a locking ring (6-6);

b. adjusting the position of a pull rope reeling device (9) on the ground, till a pull rope (4) is perpendicular to the guide rope (1);

c. winding the pull rope (4) on the pull rope reeling device (9), pulling the slide device (3) to make a displacement x in the direction of the pull rope, and logging the tension $f_1$ on a tension sensor (5) mounted on the tension rope (2) and the tension $f_2$ on a tension sensor (5) mounted on the pull rope (4);

d. calculating the tension F on the guide rope (1) with a formula $F = f_2 \cdot l/(4x) - f_1$.

* * * * *